United States Patent
Rawat (10) Patent No.: US 11,813,149 B2
(45) Date of Patent: Nov. 14, 2023

(54) FEMININE HYGIENE PAD WITH NONWOVEN TOPSHEET HAVING ENHANCED SKIN FEEL

(71) Applicant: The Procter & Gamble Company, Cincinnati, OH (US)

(72) Inventor: Digvijay Rawat, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 860 days.

(21) Appl. No.: 16/789,516

(22) Filed: Feb. 13, 2020

(65) Prior Publication Data

US 2020/0253793 A1    Aug. 13, 2020

Related U.S. Application Data

(60) Provisional application No. 62/804,864, filed on Feb. 13, 2019.

(51) Int. Cl.
| | | |
|---|---|---|
| *A61F 13/15* | (2006.01) | |
| *A61F 13/511* | (2006.01) | |
| *A61F 13/47* | (2006.01) | |
| *A61F 13/531* | (2006.01) | |

(Continued)

(52) U.S. Cl.
CPC ........ *A61F 13/51121* (2013.01); *A61F 13/47* (2013.01); *A61F 13/531* (2013.01); *A61F 2013/51019* (2013.01); *A61F 2013/51026* (2013.01); *A61F 2013/51033* (2013.01);

(Continued)

(58) Field of Classification Search
CPC .. A61F 13/51121; A61F 13/47; A61F 13/531; A61F 2013/51019; A61F 2013/51026; A61F 2013/51038; A61F 2013/530817
See application file for complete search history.

(56) References Cited

U.S. PATENT DOCUMENTS

| | | |
|---|---|---|
| 5,817,704 A | 10/1998 | Shiveley |
| 9,504,613 B2 | 11/2016 | Geilich et al. |
| 10,646,381 B2 | 5/2020 | Arora et al. |

(Continued)

FOREIGN PATENT DOCUMENTS

| | | |
|---|---|---|
| CN | 107072840 A | 8/2017 |
| CN | 109069322 A | 12/2018 |

(Continued)

OTHER PUBLICATIONS

International Search Report and Written Opinion; Application No. PCT/US2020/017826; dated Jun. 9, 2020, 13 pages.

*Primary Examiner* — Jacqueline F Stephens
(74) *Attorney, Agent, or Firm* — Sarah M. DeCristofaro (57) ABSTRACT

A feminine hygiene pad having a topsheet including a fibrous nonwoven web material having hydrophilic fibers, and an absorbent layer including an open-celled foam formed through polymerization of a high internal phase emulsion (HIPE) is disclosed. The topsheet and the absorbent layer are disposed in direct face-to-face relationship with each other, and attached to each other within a bonding region. Within the bonding region, each first identifiable point of attachment between the topsheet and the absorbent layer has a neighboring second identifiable point of attachment between the topsheet and the absorbent layer within a 6 mm radius of the first identifiable point of attachment.

15 Claims, 4 Drawing Sheets

(51) Int. Cl.
  *A61F 13/51*   (2006.01)
  *A61F 13/53*   (2006.01)

(52) U.S. Cl.
  CPC .............. *A61F 2013/51038* (2013.01); *A61F 2013/530817* (2013.01)

(56)   References Cited

U.S. PATENT DOCUMENTS

| | | |
|---|---|---|
| 2003/0191442 A1 | 10/2003 | Bewick-sonntag et al. |
| 2004/0087924 A1 | 5/2004 | Sroda |
| 2011/0130734 A1 | 6/2011 | Carlucci |
| 2013/0116646 A1* | 5/2013 | Robles ................... A61L 15/26 604/378 |
| 2016/0167334 A1 | 6/2016 | Arora |
| 2017/0319403 A1* | 11/2017 | Bewick-Sonntag .... A61F 13/47 |

FOREIGN PATENT DOCUMENTS

| | | |
|---|---|---|
| CN | 109069327 A | 12/2018 |
| CN | 109069329 A | 12/2018 |
| JP | 2015037479 A | 2/2015 |

* cited by examiner

FEMININE HYGIENE PAD WITH NONWOVEN TOPSHEET HAVING ENHANCED SKIN FEEL

CROSS REFERENCE TO RELATED APPLICATION

This application claims the benefit of U.S. Provisional Application No. 62/804,864, filed Feb. 13, 2019, the substance of which is incorporated herein by reference.

BACKGROUND OF THE INVENTION

Through experience and consumer research it has been learned that users of feminine hygiene pads have developed a number of varying expectations and preferences for such products, as the products themselves have evolved. These expectations and preferences include (in no particular order) (1) that the pad feel soft, breathable and comfortable against the skin when dry, prior to a discharge of menstrual fluid; (2) that the pad not feel overly wet (i.e., that it remain somewhat or substantially dry-feeling) against the skin following a discharge of fluid; (3) that the pad have suitable absorption performance such that it will readily accept, absorb, contain, isolate and effectively retain menstrual fluid discharged, away from the user's skin and without leaking, over a normal time of use/wear; (4) that the pad at least somewhat conceal absorbed fluid, such that, on the outward-facing surfaces, it does not present overly dark coloration that may be visible through outer clothing, and on the wearer-facing surfaces, provides visual suggestion that absorbed fluid is contained and isolated from the wearer's skin; (5) that the pad be as thin (non-bulky), flexible and pliable as possible for purposes of comfort, accommodation of the wearer's body movements, and discreetness of wear under clothing; and (6) that the pad not substantially support the presence or growth of microorganisms near the skin or genital area during the time of use/wear. With respect to currently known product designs and the materials currently known and used as components of these products, these expectations and preferences cannot all be fully met simultaneously. The manufacturer must carefully balance its priorities, to provide product features that address each of these expectations and preferences to greater and lesser extents under competitive cost/pricing constraints, in order to provide a product that will sufficiently please its user/consumer market.

Many currently marketed feminine hygiene pads have topsheets formed of apertured film. Polymeric film (often polyethylene-based film) has been found suitable as a topsheet material for many consumers because it is not substantially absorbent and therefore does not retain deposited fluid; it tends to remain somewhat dry-feeling following a discharge of fluid and subsequent absorption by absorbent components below. The typical film topsheet is provided with a pattern of apertures through the film, of a size, geometry and numerical density per unit surface area to provide sufficient passageways through the film, through which the discharged fluid may pass to absorbent material beneath the topsheet. In some examples the apertures may be formed via a vacuum-forming process that imparts a small flexible funnel-like structure to each aperture, causing it to function in a manner akin to a one-way check valve. However, some consumers may negatively perceive the feel of "plastic" against the skin.

Nonwovens of suitable basis weights and formed of polymeric fibers may provide a more preferred feel against the skin than film for some users when dry, but unless treated to be hydrophilic, do not readily accept or wick aqueous fluid through them so that it can be absorbed by an absorbent structure below. To address this issue such a nonwoven may be apertured by various processes. However, an apertured nonwoven may have mechanical weakness or dimensional instability (negatively affecting processability on a manufacturing line) and/or may not provide a desirable level of visual concealment of absorbed fluid. Further, the relatively larger apertures required for such a nonwoven may permit bits of dislodged absorbent materials within the absorbent structure beneath to sift through and out of the apertures, which may contribute to negative consumer perceptions of quality.

Normally hydrophobic polymer fibers may be treated to render them hydrophilic, and used to form a nonwoven web for a topsheet material, without the need for apertures to admit and facilitate movement of fluid therethrough. Normally hydrophilic fibers (such, for example, suitably processed cotton fibers and rayon fibers) may be used to form a nonwoven web for a topsheet material, also without the need for apertures. These may have a more pleasant feel against the skin for some consumers when dry, as compared to an apertured film. Further, materials such as cotton or other plant fibers have appeal for some consumers for use as components of skin-contacting materials, because they are deemed natural products. Nonwovens formed of hydrophilic fibers, suitably manufactured, can readily accept and internally disperse discharged menstrual fluid (which is aqueous) via a wicking action. Nonwovens formed of hydrophilic fibers, however, may retain and thereby not pass all discharged fluid through to the absorbent material beneath, or may be prone to rewetting (reacquisition of fluid from the absorbent material beneath). Because the constituent fibers are hydrophilic, the nonwoven tends to attract and/or retain some portion of the discharged fluid, i.e., it is functionally part of the absorbent structure, rather than more desirably serving as a barrier between the wearer and the absorbed fluid, with one-way passageways to admit and conduct discharged fluid through to the absorbent structure beneath. Thus, a topsheet formed of hydrophilic fibers may, undesirably, feel wet against the wearer's skin following a discharge of fluid, and may not provide substantial concealment of absorbed fluid because it retains some fluid itself. Further, a wet topsheet may provide a medium that will support presence or growth of microorganisms at a location proximate the wearer's skin and genital area, which is generally deemed undesirable.

Thus, there remains room for improvement in combinations of topsheet materials, absorbent materials and pad structures that enable the manufacturer to successfully satisfy more user/consumer expectations and preferences than are currently known.

DETAILED DESCRIPTION OF THE INVENTION

Definitions

With respect to a feminine hygiene pad that is opened and laid out flat on a horizontal planar surface, "lateral" refers to a direction perpendicular to the longitudinal direction and parallel the horizontal planar surface.

With respect to a feminine hygiene pad that is opened and laid out flat on a horizontal planar surface and having a length measured from forward end to rearward end, "longitudinal" refers to a direction parallel with the line along which the length is measured, and parallel to the horizontal planar surface. "Length" refers to a dimension measured in the longitudinal direction.

With respect to a feminine hygiene pad, the terms "front," "rear," "forward" and "rearward" relate to features or regions of the pad corresponding to the position it would occupy as ordinarily worn by a user, and the front and rear of the user's body when standing.

With respect to a feminine hygiene pad that is opened and laid out flat on a horizontal planar surface, or a nonwoven web material laid out flat on a horizontal planar surface, "z-direction" refers to a direction perpendicular to the horizontal planar surface, and any plane parallel to the horizontal planar surface may be referred to as an "x-y plane". When the pad is being worn by a user (and thus has been urged into a curving configuration), "z-direction" at any particular point location on the pad refers to a direction normal to the wearer-facing surface of the pad at the particular point location. With respect to a nonwoven web during its manufacture, "z-direction" refers to a direction orthogonal to both the machine direction and the cross direction of manufacture, and any plane parallel to the machine direction and cross direction may be referred to as an "x-y plane".

With respect to a feminine hygiene pad, "wearer-facing" is a relative locational term referring to a feature of a component or structure of the pad that when in use that lies closer to the wearer than another feature of the component or structure that lies along the same z-direction. For example, a topsheet has a wearer-facing surface that lies closer to the wearer than the opposite, outward-facing surface of the topsheet.

With respect to a feminine hygiene pad, "outward-facing" is a relative locational term referring to a feature of a component or structure of the pad that when in use that lies farther from the wearer than another feature of the component or structure that lies along the same z-direction. For example, a topsheet has an outward-facing surface that lies farther from the wearer than the opposite, wearer-facing surface of the topsheet.

Description

Figure 1:
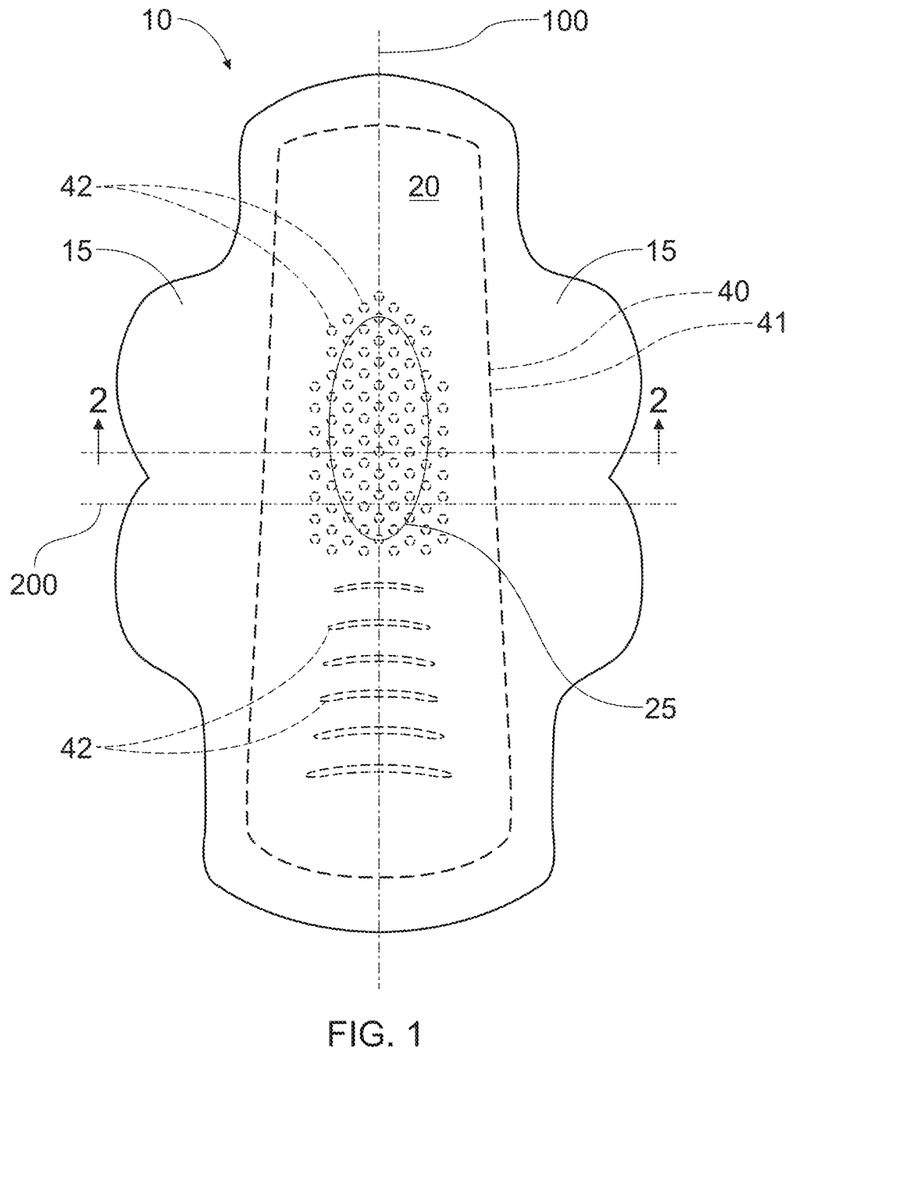
FIG. 1 is a plan view of a feminine hygiene pad, topsheet side facing the viewer.
Figure 2A:
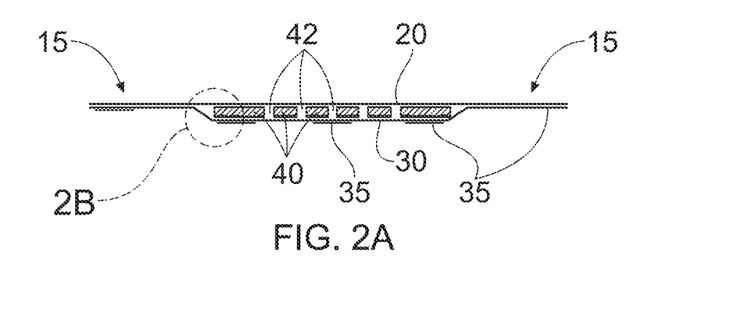
FIG. 2A is a schematic lateral cross section of the feminine hygiene pad of FIG. 1.

Referring to FIGS. 1 and 2A, a feminine hygiene pad 10 may include a liquid permeable topsheet 20, a liquid impermeable backsheet 30 and an absorbent layer 40 disposed between the topsheet and the backsheet. The absorbent layer has an outer perimeter 41. In regions outside the outer perimeter 41, the topsheet and the backsheet may be bonded together in laminated fashion by any suitable mechanism including but not limited to adhesive bonding, thermal bonding, pressure bonding, etc., thereby retaining and holding the absorbent layer 40 in place between the topsheet 20 and the backsheet 30. Pad 10 may include opposing wing portions 15 extending laterally outside of perimeter 41 by a comparatively greater width dimension than the main portion of the pad. The outer surface of the backsheet forming the undersides of the main portion and the wing portions may have deposits of adhesive 35 thereon. Adhesive deposits 35 may be provided to enable the user to adhere the pad to the inside of her underpants in the crotch region thereof, and wrap the wing portions through and around the inside edges of the leg openings of the underpants and adhere them to the outside/underside of the underpants in the crotch region, providing supplemental holding support and helping guard the leg edges of the underpants against soiling. When pad 10 is packaged, adhesive deposits 35 may be covered by one or more sheets of release film or paper (not shown) that covers/shields the adhesive deposits 35 from contact with other surfaces until the user is ready to remove the release film or paper and place the pad for use.

Topsheet

Topsheet 20 may be formed of any suitable hydrophilic nonwoven web material. Referring back to the figures, the topsheet 20 is positioned adjacent a wearer-facing surface of the absorbent layer 40 and may be joined thereto and to the backsheet 30 by any suitable attachment or bonding method. The topsheet 20 and the backsheet 30 may be joined directly to each other in the peripheral regions outside the perimeter 41 of the absorbent layer 40 and may be indirectly joined by directly joining them respectively to wearer-facing and outward-facing surfaces of the absorbent layer or additional optional layers included with the pad.

The pad 10 may have any known or otherwise effective topsheet, such as one which is compliant, soft feeling, and non-irritating to the wearer's skin. A suitable topsheet material will include a liquid pervious material that is comfortable when in contact with the wearer's skin and permits discharged menstrual fluid to rapidly penetrate through it. A suitable topsheet may be made of various materials such as woven and nonwoven web materials.

Nonlimiting examples of nonwoven web materials that may be suitable for use as the topsheet include fibrous materials made from natural fibers, modified natural fibers, synthetic fibers, or combinations thereof. Some suitable examples are described in U.S. Pat. Nos. 4,950,264; 4,988,344; 4,988,345; 3,978,185; 7,785,690; 7,838,099; 5,792,404; and 5,665,452.

In some examples, the topsheet may comprise tufts as described in U.S. Pat. Nos. 8,728,049; 7,553,532; 7,172,801; 8,440,286; 7,648,752; and 7,410,683. The topsheet may have a pattern of discrete hair-like fibrils as described in U.S. Pat. No. 7,655,176 or 7,402,723. Additional examples of suitable topsheet materials include those described in U.S. Pat. Nos. 8,614,365; 8,704,036; 6,025,535 and US 2015/041640. Another suitable topsheet may be formed from a three-dimensional substrate as detailed in US 2017/0258647. The topsheet may have one or more layers, as described in US 2016/0167334; US 2016/0166443; and US 2017/0258651.

As contemplated herein, component nonwoven web material from which topsheet 20 may be cut may be a nonwoven web material that includes or consists predominately (by weight) or entirely of cellulosic plant fibers such as fibers of cotton, flax, hemp, jute or mixtures thereof, that are either naturally hydrophilic or suitably processed so as be rendered hydrophilic (or have increased hydrophilicity), and processed to be suitably soft-feeling against the skin. Plant-based fibers may be preferred, to appeal to consumer preferences for natural products. In other examples, semisynthetic fibers derived from cellulosic material, such as rayon (including viscose, lyocell, MODAL (a product of Lenzing AG, Lenzing, Austria) and cuprammonium rayon) may be used.

The nonwoven web may be formed via any suitable process by which fibers of finite lengths may be distributed and accumulated in a controlled fashion onto a forming belt to form a batt having a desired distribution of fibers, to a desired basis weight. Suitable processes may include carding, airlaying and wetlaying. The batt may be processed to consolidate the fibers and entangle them in the z-direction, by processes that may include calendering, needlepunching and hydroentanglement via water jets.

In some examples a topsheet cut from a nonwoven including or consisting predominately (by weight) or entirely of plant fibers, such as cotton fibers, may be preferred. In some examples, the nonwoven web material may be formed via a carding process. In other examples, the nonwoven web material may be formed via an airlaying or wetlaying process. In still other examples the nonwoven web material may be formed in a co-forming process in which plant-based fibers of finite lengths are physically blended or mixed with streams of spun fibers of longer but indefinite lengths, spun from polymeric resin, and laid down on a forming belt to form a web as described in, for example, U.S. Pat. Nos. 8,017,534; 4,100,324; US 2003/0200991; U.S. Pat. No. 5,508,102; US 2003/0211802; EP 0 333 228; WO 2009/10938; US 2017/0000695; US 2017/0002486; U.S. Pat. No. 9,944,047; 2017/0022643 and US 2018/0002848.

In order to ensure that fluid contacting the top (wearer-facing) surface of a hydrophilic topsheet will move suitably rapidly via capillary action in a z-direction to the bottom (outward-facing) surface of the topsheet where it can be drawn into the absorbent layer, it may be important to ensure that the nonwoven web material forming the topsheet has an appropriate weight/volume density, reflecting suitable presence of interstitial passageways among and between the constituent fibers, through which fluid may move within the nonwoven material. A nonwoven with fibers that are consolidated too densely will have insufficient numbers and volume of interstitial passageways, and the nonwoven will obstruct rather than facilitate rapid z-direction fluid movement. On the other hand, a nonwoven with fibers that are not consolidated enough to provide sufficient fiber-to-fiber contact and/or sufficiently small interstitial passageways may provide insufficient potential for wicking in the z-direction via capillary action. In examples in which the nonwoven web material includes or consists predominately or entirely of cotton fibers, for purposes of balancing priorities of absorbed fluid concealment and mechanical strength (needed for processing), versus limiting the quantity of topsheet material through which liquid must move in the z-direction to reach the absorbent layer beneath, it may be desired that the web have a basis weight of 20 gsm (herein, "gsm" means grams/m$^2$) to 50 gsm, more preferably 25 gsm to 45 gsm, and even more preferably 30 gsm to 40 gsm. In conjunction, it may be desired that the web have a density of 74 kg/m$^3$ to 110 kg/m$^3$ and more preferably 83 kg/m$^3$ to 101 kg/m$^3$, where density is calculated as basis weight divided by caliper (z-direction thickness, measured using the caliper measurement method set forth below). Alternatively, or in combination with control of the values above, the caliper of the topsheet material may be controlled, to balance competing needs for opacity and loft (which call for a higher caliper) vs. a limitation on the z-direction distance that discharged fluid must travel through the topsheet from the wearer-facing surface to the outward-facing surface, to reach the absorbent layer below. Thus, it may be desired that the manufacture of the topsheet material be controlled to produce a topsheet material having a caliper of 0.20 mm to 0.60 mm, more preferably 0.25 mm to 0.55 mm, and even more preferably 0.30 mm to 0.45 mm. For purposes herein, caliper is measured using the caliper measurement method set forth below.

Immediately following separation from the bolls, cotton fiber is naturally hydrophobic due to the presence of natural waxy and oily compounds on the surfaces of the fibers. After ginning to separate the cotton fiber from the seeds, masses of raw cotton fiber (stored and transported in bales) typically include substantial quantities of impurities (particulates, bits of plant matter, etc.), trapped within the fibrous matrices and/or adhered to the waxes and oils, that both discolor the cotton fiber and make it unsuitable for many uses. In order to make raw cotton fiber commercially acceptable for most uses, the fiber must first be processed in several steps to remove the impurities. Typical processes also remove the natural waxes and oils and render the cotton fiber hydrophilic. Hydrophobizing agents such as oils, waxes or silicones can be reintroduced to render the cotton fibers and cotton-based fibrous structure hydrophobic and nonabsorbent, but for purposes herein an unapertured hydrophobic cotton-based topsheet would be unsuitable because it would not suitably accept and wick a discharge of fluid.

Following processing to remove impurities a mass of cotton fiber will be further mechanically processed to convert it to its intended end use condition and structure. Due to its hydrophilic nature, any mass of processed cotton fiber—whether appearing as a component of a textile/cloth, a paper product, a nonwoven web product or an absorbent product, will be absorbent of aqueous fluid to some extent, and will exhibit capillary wicking properties.

Rayon (including viscose, lyocell, tencel, cuprammonium rayon, etc.) fiber is manufactured from regenerated cellulose. At a molecular level, it is chemically similar to cotton fiber. At the fiber level rayon fiber can be imparted with complex surface geometry and substantial curl or crimp, and is naturally hydrophilic. Masses of rayon fiber typically have absorbency properties exceeding those of masses of cotton fiber.

Absorbency and wicking performance may vary according to, and may be manipulated by, the manner in which the fiber is further processed. Factors such as level of consolidation (i.e., densification) of the fiber mass in the end structure and orientations of the individual fibers within the end structure can affect absorbency and wicking performance.

Thus, for purposes contemplated herein, in combination with being imparted with a suitable basis weight, density and/or caliper as discussed above, it may be desired that a cotton- and/or rayon-based nonwoven web used to make the topsheet be formed via a nonwoven web manufacturing process in which substantial numbers of the fibers are imparted with directional orientation that includes some z-direction orientation, rather than orientations predominately biased along the machine direction or x-y plane of formation of the web structure. Following any suitable processes in which fibers are distributed and laid down in a batt on a horizontal forming belt (e.g., airlaying, wetlaying, carding, etc.), additional process steps that forcibly reorient some of the fibers or portions thereof in the z-direction may be employed. Suitable process steps may include needlepunching and hydroentangling. Hydroentangling, in which an array of fine, high-velocity water jets are directed at the batt as it is conveyed past them on a foraminous belt or drum, may be desired for its effectiveness in reorienting fibers while breaking fewer fibers and creating less broken fiber lint and surface fuzz (free fiber ends extending from the main structure of the web). A vacuum water removal system (in which air is drawn through the web in a z-direction into and through a pattern of orifices or pores on a drum or belt conveying the batt, pulling the hydrojetted water with it) may be desired because it tends to create, add, open and/or clear small z-direction passageways within the fiber matrix of the web, approximately in the pattern of the orifices or pores. Without intending to be bound by theory, it is believed that an increased number of fibers (or portions thereof) oriented in the z-direction, and the z-direction passageways, increase the ability and tendency of the web to wick aqueous fluid in the z-direction. In a topsheet, this would mean that the material can more readily wick aqueous fluid from the wearer-facing surface of the topsheet to the outward-facing surface of the topsheet, i.e., directly down to the absorbent layer below, and may thereby wick fluid less along x-y planar directions (causing a stain from discharged fluid to spread laterally and/or longitudinally).

Absorbent Layer

In some examples the absorbent layer 40 may be formed of or include a layer of absorbent open-celled foam material. In some examples, the foam material may include at least first and second sublayers 40*a*, 40*b* (FIG. 2B) of absorbent open-celled foam material, the sublayers being in direct face-to-face contact with each other. In such examples, the wearer-facing sublayer may be a relatively larger-celled foam material, and the outward-facing sublayer may be a relatively smaller-celled foam material, for purposes explained in more detail below.

The open-celled foam material may be a foam material that is manufactured via polymerization of the continuous oil phase of a water-in-oil high internal phase emulsion ("HIPE").

A water-in-oil HIPE has two phases. One phase is a continuous oil phase comprising monomers to be polymerized, and an emulsifier to help stabilize the HIPE. The oil phase may also include one or more photoinitiators. The monomer component may be included in an amount of from about 80% to about 99%, and in certain examples from about 85% to about 95% by weight of the oil phase. The emulsifier component, which is soluble in the oil phase and suitable for forming a stable water-in-oil emulsion may be included in the oil phase in an amount of from about 1% to about 20% by weight of the oil phase. The emulsion may be formed at an emulsification temperature of from about 20° C. to about 130° C. and in certain examples from about 50° C. to about 100° C.

In general, the monomers will may be included in an amount of about 20% to about 97% by weight of the oil phase and may include at least one substantially water-insoluble monofunctional alkyl acrylate or alkyl methacrylate. For example, monomers of this type may include C4-C18 alkyl acrylates and C2-C18 methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also include from about 2% to about 40%, and in certain examples from about 10% to about 30%, by weight of the oil phase, a substantially water-insoluble, polyfunctional crosslinking alkyl acrylate or methacrylate. This crosslinking comonomer, or crosslinker, is added to confer strength and resilience to the resulting HIPE foam. Examples of crosslinking monomers of this type comprise monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,1 2-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of crosslinkers contain a mixture of acrylate and methacrylate moieties, such as ethylene glycol acrylate-methacrylate and neopentyl glycol acrylate-methacrylate. The ratio of methacrylate:acrylate group in the mixed crosslinker may be varied from 50:50 to any other ratio as needed.

Any third substantially water-insoluble comonomer may be added to the oil phase in weight percentages of from about 0% to about 15% by weight of the oil phase, in certain examples from about 2% to about 8%, to modify properties of the HIPE foams. In certain cases, "toughening" monomers may be desired to impart toughness to the resulting HIPE foam. These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better-formed HIPE foam which results in greater toughness, tensile strength, abrasion resistance, and the like. Monomers may also be added to confer flame retardancy, as disclosed, for example, in U.S. Pat. No. 6,160,028. Monomers may be added to impart color (for example vinyl ferrocene); to impart fluorescent properties; to impart radiation resistance; to impart opacity to radiation (for example lead tetraacrylate); to disperse charge; to reflect incident infrared light; to absorb radio waves; to make surfaces of the HIPE foam struts or cell walls wettable; or for any other desired property in a HIPE foam. In some cases, these additional monomers may slow the overall process of conversion of HIPE to HIPE foam, the tradeoff being necessary if the desired property is to be conferred. Thus, such monomers can also be used to slow down the polymerization rate of a HIPE. Examples of monomers of this type comprise styrene and vinyl chloride.

The oil phase may further include an emulsifier to stabilize the HIPE. Emulsifiers used in a HIPE can include: (a) sorbitan monoesters of branched C16-C24 fatty acids; linear unsaturated C16-C22 fatty acids; and linear saturated C12-C14 fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of -branched C16-C24 fatty acids, linear unsaturated C16-C22 fatty acids, or linear saturated C12-C14 fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched C16-C24 alcohols, linear unsaturated C16-C22 alcohols, and linear saturated C12-C14 alcohols, and mixtures of these emulsifiers. See U.S. Pat. Nos. 5,287,207 and 5,500,451. Another emulsifier that may be used is polyglycerol succinate (PGS), which is formed from an alkyl succinate, glycerol, and triglycerol.

Such emulsifiers, and combinations thereof, may be added to the oil phase so that they constitute about 1% to about 20%, in certain examples about 2% to about 15%, and in certain other examples about 3% to about 12%, of the weight of the oil phase. In certain examples, coemulsifiers may also be used to provide additional control of cell size, cell size distribution, and emulsion stability, particularly at higher temperatures, for example greater than about 65° C. Examples of coemulsifiers include phosphatidyl cholines and phosphatidyl choline-containing compositions, aliphatic betaines, long chain C12-C22 dialiphatic quaternary ammonium salts, short chain C1-C4 dialiphatic quaternary ammonium salts, long chain C12-C22 dialkoyl(alkenoyl)-2-hydroxyethyl, short chain C1-C4 dialiphatic quaternary ammonium salts, long chain C12-C22 dialiphatic imidazolinium quaternary ammonium salts, short chain C1-C4 dialiphatic imidazolinium quaternary ammonium salts, long chain C12-C22 monoaliphatic benzyl quaternary ammonium salts, long chain C12-C22 dialkoyl(alkenoyl)-2-aminoethyl, short chain C1-C4 monoaliphatic benzyl quaternary ammonium salts, short chain C1-C4 monohydroxyaliphatic quaternary ammonium salts. In certain examples, ditallow dimethyl ammonium methyl sulfate (DTDMAMS) may be used as a coemulsifier.

Any photoinitiators included may be included at between about 0.05% and about 10%, and in some examples between about 0.2% and about 10% by weight of the oil phase. Lower amounts of photoinitiator allow light to better penetrate the HIPE foam, which can provide for polymerization deeper into the HIPE foam. However, if polymerization is performed in an oxygen-containing environment, it may be desired that there be enough photoinitiator present to initiate the polymerization and overcome oxygen inhibition. Photoinitiators can respond rapidly and efficiently to a light source with the production of radicals, cations, and other species that are capable of initiating a polymerization reaction. Photoinitiators selected for use in forming foams within contemplation of the present disclosure may absorb UV light at wavelengths of about 200 nanometers (nm) to about 800 nm, in certain examples about 250 nm to about 450 nm. If the photoinitiator is in the oil phase, suitable types of oil-soluble photoinitiators include benzyl ketals, α-hydroxyalkyl phenones, α-amino alkyl phenones, and acylphospine oxides. Examples of photoinitiators include 2,4,6-[trimethylbenzoyldiphosphine]oxide in combination with 2-hydroxy-2-methyl-1-phenylpropan-1-one (50:50 blend of the two is sold by Ciba Speciality Chemicals, Ludwigshafen, Germany as DAROCUR® 4265); benzyl dimethyl ketal (sold by Ciba Geigy as IRGACURE 651); α-,α-dimethoxy-α-hydroxy acetophenone (sold by Ciba Speciality Chemicals as DAROCUR® 1173); 2-methyl-1-[4-(methyl thio)phenyl]-2-morpholino-propan-1-one (sold by Ciba Speciality Chemicals as IRGACURE® 907); 1-hydroxycyclohexyl-phenyl ketone (sold by Ciba Speciality Chemicals as IRGACURE® 184); bis(2,4,6-trimethylbenzoyl)-phenylphosphineoxide (sold by Ciba Speciality Chemicals as IRGACURE 819); diethoxyacetophenone, and 4-(2-hydroxyethoxy)phenyl-(2-hydroxy-2-methylpropyl) ketone (sold by Ciba Speciality Chemicals as IRGACURE® 2959); and Oligo [2-hydroxy-2-methyl-1-[4-(1-methylvinyl)phenyl]propanone] (sold by Lamberti spa, Gallarate, Italy as ESACURE® KIP EM.

The dispersed aqueous phase of a HIPE comprises water, and may also comprise one or more components, such as initiator, photoinitiator, or electrolyte, wherein in certain examples, the one or more components are at least partially water soluble.

One component included in the aqueous phase may be a water-soluble electrolyte. The water phase may contain from about 0.2% to about 40%, in certain examples from about 2% to about 20%, by weight of the aqueous phase of a water-soluble electrolyte. The electrolyte minimizes the tendency of monomers, comonomers, and crosslinkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte can include a buffering agent for the control of pH during the polymerization, including such inorganic counterions as phosphate, borate, and carbonate, and mixtures thereof. Water soluble monomers may also be used in the aqueous phase, examples being acrylic acid and vinyl acetate.

Another component that may be included in the aqueous phase is a water-soluble free-radical initiator. The initiator can be present at up to about 20 mole percent based on the total moles of polymerizable monomers present in the oil phase. In certain examples, the initiator may be included in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethyleneisobutyramidine)dihydrochloride, azo initiators, redox couples like persulfate-bisulfite, persulfate-ascorbic acid, and other suitable redox initiators. In certain examples, to reduce the potential for premature polymerization which may clog the emulsification system, addition of the initiator to the monomer phase may be performed near the end of the emulsification step, or shortly afterward.

Photoinitiator, if included in the aqueous phase, may be at least partially water soluble, and may constitute between about 0.05% and about 10%, and in certain examples between about 0.2% and about 10%, by weight of the oil phase. Lower amounts of photoinitiator allow light to better penetrate the HIPE foam, which can provide for polymerization deeper into the HIPE foam. However, if polymerization is done in an oxygen-containing environment, there should be enough photoinitiator to initiate the polymerization and overcome oxygen inhibition. Photoinitiators can respond rapidly and efficiently to a light source with the production of radicals, cations, and other species that are capable of initiating a polymerization reaction. Photoinitiators selected for use to form foams within contemplation of the present disclosure may absorb UV light at wavelengths of from about 200 nanometers (nm) to about 800 nm, in certain examples from about 200 nm to about 350 nm, and in certain examples from about 350 nm to about 450 nm. If a photoinitiator is to be included in the aqueous phase, suitable types of water-soluble photoinitiators may include benzophenones, benzils, and thioxanthones. Examples of photoinitiators include 2,2'-Azobis[2-(2-imidazolin-2-yl) propane]dihydrochloride; 2,2'-Azobis[2-(2-imidazolin-2-yl) propane]disulfate dehydrate; 2,2'-Azobis(1-imino-1-pyrrolidino-2-ethylpropane)dihydrochloride; 2,2'-Azobis[2-methyl-N-(2-hydroxyethyl)propionamide]; 2,2'-Azobis(2-methylpropionamidine)dihydrochloride; 2,2'-dicarboxymethoxydibenzalacetone, 4,4'- dicarboxymethoxydibenzalacetone, 4,4'-dicarboxymethoxydibenzalcyclohexanone, 4-dimethylamino-4'-carboxymethoxydibenzalacetone; and 4,4'-disulphoxymethoxydibenzalacetone. Other suitable photoinitiators that can be used are listed in U.S. Pat. No. 4,824,765.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler particles, for example starch, titanium dioxide, carbon black, or calcium carbonate; fibers; chain transfer agents; odor absorbers, for example activated carbon particulates; dissolved polymers; dissolved oligomers; and the like.

HIPE foam is produced from the polymerization of the monomers comprising the continuous oil phase of a HIPE. In certain examples, a HIPE foam layer may have one or more sublayers, and may be either homogeneous or heterogeneous polymeric open-celled foams. Homogeneity and heterogeneity relate to distinct layers within the same HIPE foam, which are similar in the case of homogeneous HIPE foams and differ in the case of heterogeneous HIPE foams. A heterogeneous HIPE foam may contain at least two distinct sublayers that differ with regard to their chemical composition, physical properties, or both; for example, sublayers may differ with regard to one or more of foam density, polymer composition, specific surface area, or pore size (also referred to as cell size). For example, for a HIPE foam if the difference relates to pore size, the average pore size in the respective sublayers may differ by at least about 20%, in certain examples by at least about 35%, and in still other examples by at least about 50%. In another example, if the differences in the sublayers of a HIPE foam layer relate to density, the densities of the layers may differ by at least about 20%, in certain examples by at least about 35%, and in still other examples by at least about 50%. For instance, if one layer of a HIPE foam has a density of 0.020 g/cm$^3$, another layer may have a density of at least about 0.024 g/cm3 or less than about 0.016 g/cm3, in certain examples at least about 0.027 g/cm$^3$ or less than about 0.013 g/cm$^3$, and in still other examples at least about 0.030 g/cm$^3$ or less than about 0.010 g/cm$^3$. If the differences between the layers are related to the chemical composition of the HIPE or HIPE foam, the differences may reflect a relative amount difference in at least one monomer component, for example by at least about 20%, in certain examples by at least about 35%, and in still further examples by at least about 50%. For instance, if one sublayer of a HIPE or HIPE foam is composed of about 10% styrene in its formulation, another sublayer of the HIPE or HIPE foam may be composed of at least about 12%, and in certain examples of at least about 15%.

A HIPE foam layer structured to have distinct sublayers formed from differing HIPEs may provide a HIPE foam layer with a range of desired performance characteristics. For example, a HIPE foam layer comprising first and second foam sublayers, wherein the first foam sublayer has a relatively larger pore or cell size, than the second sublayer, when used in an absorbent article may more quickly absorb incoming fluids than the second sublayer. For example, when the HIPE foam layer is used to form an absorbent layer of a feminine hygiene pad, the first foam sublayer may be layered over the second foam sublayer having relatively smaller pore sizes, as compared to the first foam sublayer, which exert more capillary pressure and draw the acquired fluid from the first foam sublayer, restoring the first foam sublayer's ability to acquire more fluid from above. HIPE foam pore sizes may range from 1 to 200 µm and in certain examples may be less than 100 µm. HIPE foam layers of the present disclosure having two major parallel surfaces may be from about 0.5 to about 10 mm thick, and in certain examples from about 2 to about 10 mm. The desired thickness of a HIPE foam layer will depend on the materials used to form the HIPE foam layer, the speed at which a HIPE is deposited on a belt, and the intended use of the resulting HIPE foam layer.

The HIPE foam layers of the present disclosure are relatively open-celled. This refers to the individual cells or pores of the HIPE foam layer being in substantially unobstructed communication with adjoining cells. The cells in such substantially open-celled HIPE foam structures have intercellular openings or windows that are large enough to permit ready fluid transfer from one cell to another within the HIPE foam structure. For purpose of the present disclosure, a HIPE foam is considered "open-celled" if at least about 80% of the cells in the HIPE foam that are at least 1 µm in size are in fluid communication with at least one adjoining cell.

In addition to being open-celled, in certain examples HIPE foams are adapted to be sufficiently hydrophilic to permit the HIPE foam to absorb aqueous fluids. In some examples the internal surfaces of a HIPE foam may be rendered hydrophilic by residual hydrophilizing surfactants or salts left in the HIPE foam following polymerization, or by selected post-polymerization HIPE foam treatment procedures such as those as described in references cited herein.

In certain examples, for example when it is used to form an absorbent layer of a feminine hygiene pad, a HIPE foam layer may be flexible and exhibit an appropriate glass transition temperature (Tg). The Tg represents the midpoint of the transition between the glassy and rubbery states of the polymer. In general, HIPE foams that have a Tg that is higher than the temperature of use can be strong but will also be relatively rigid and potentially prone to fracture (brittle). In certain examples, regions of the HIPE foams of the current disclosure which exhibit either a relatively high Tg or excessive brittleness will be discontinuous. Since these discontinuous regions will also generally exhibit high strength, they can be prepared at lower densities without compromising the overall strength of the HIPE foam.

HIPE foams intended for applications requiring flexibility should contain at least one continuous region having a Tg as low as possible, so long as the overall HIPE foam has acceptable strength at in-use temperatures. In certain examples, the Tg of this region will be less than about 40° C. for foams used at about ambient temperature conditions; in certain other examples Tg will be less than about 30° C. For HIPE foams used in applications wherein the use temperature is higher or lower than ambient temperature, the Tg of the continuous region may be no more than 10° C. greater than the use temperature, in certain examples the same as use temperature, and in further examples about 10° C. less than use temperature wherein flexibility is desired. Accordingly, monomers are selected as much as possible that provide corresponding polymers having lower Tg's.

HIPE foams useful for forming absorbent layers and/or sublayers within contemplation of the present disclosure, and materials and methods for their manufacture, also include but are not necessarily limited to those foams and methods described in U.S. Pat. Nos. 10,045,890; 9,056,412; 8,629,192; 8,257,787; 7,393,878; 6,551,295; 6,525,106; 6,550,960; 6,406,648; 6,376,565; 6,372,953; 6,369,121; 6,365,642; 6,207,724; 6,204,298; 6,158,144; 6,107,538; 6,107,356; 6,083,211; 6,013,589; 5,899,893; 5,873,869; 5,863,958; 5,849,805; 5,827,909; 5,827,253; 5,817,704; 5,817,081; 5,795,921; 5,741,581; 5,652,194; 5,650,222; 5,632,737; 5,563,179; 5,550,167; 5,500,451; 5,387,207; 5,352,711; 5,397,316; 5,331,015; 5,292,777; 5,268,224; 5,260,345; 5,250,576; 5,149,720; 5,147,345; and US 2005/0197414; US 2005/0197415; US 2011/0160326; US 2011/0159135; US 2011/0159206; US 2011/0160321; and US 2011/0160689, which are incorporated herein by reference to the extent not inconsistent herewith.

As reflected in FIG. 1, an absorbent layer formed of HIPE foam may include one or more patterns of perforations 42, including at least a first pattern disposed within an expected discharge location (coincidental and/or co-located with bonding region 25) overlying the intersection of longitudinal and lateral axes 100, 200 of the pad. Perforations 42 may be punched, cut or otherwise formed through the entire z-direction depth of the HIPE foam absorbent layer, or only through a wearer-facing layer or partially into the wearer-facing portion thereof. When a HIPE foam absorbent layer is disposed in direct contact with a topsheet as described herein, with no intervening acquisition layer formed of another material, perforations 42 may serve as a group of reservoirs to receive, temporarily hold, and aid in distributing rapid discharges of relatively small quantities of menstrual fluid, until the HIPE foam has sufficient time to distribute and absorb the fluid via capillary action. Additionally, such perforations help decrease bending stiffness of the absorbent layer, which may help increase comfort of the pad for the wearer. A pattern of perforations having an average radius or other largest dimension of 1.0 mm to 4.0 mm, and more preferably 1.5 mm to 3.5 mm may be included, within, for example, the area occupied by the bonding region 25. The pattern may include perforations at a numerical density of 3.0 to 9.0 perforations per $cm^2$, and more preferably 4.0 to 8.0 perforations per $cm^2$. In selecting the appropriate average size, numerical density, and surface area occupied by the pattern of perforations, the manufacturer may wish to balance the volume of the "reservoirs" desired with the need to retain absorbent material in locations proximate to and about the expected discharge location. Additional details concerning configurations of such perforations in combination with examples of suitable absorbent layers may be found in U.S. Pat. No. 8,211,078.

Figure 2B:
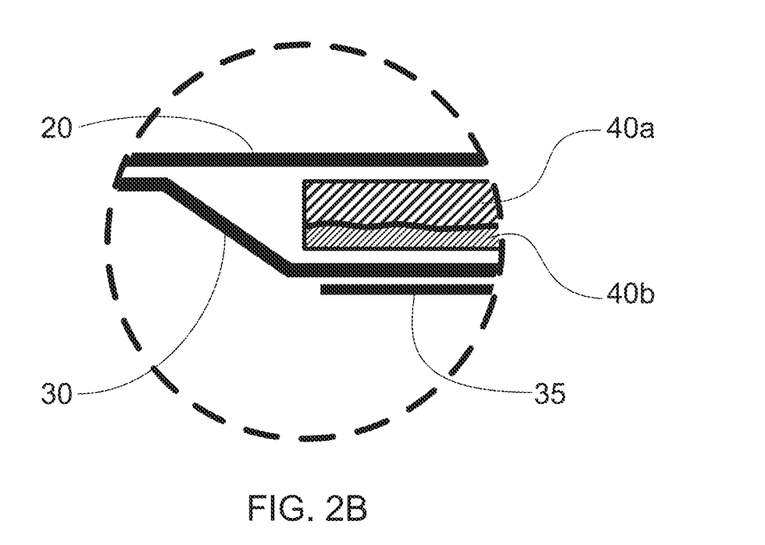
FIG. 2B is an enlarged portion 2B of the drawing of FIG. 2A, enlarged to depict sublayers of an absorbent layer.

The absorbent layer formed of HIPE foam should be imparted with sufficient CWPA (described below) to have capability to effectively draw discharged fluid from a topsheet over a time of use/wear of the pad during menstruation that is normal and expected for feminine hygiene pads, for example, from 4 to 8 hours. As noted below, the CWPA of a material is in part affected by its volume. Thus, it may be desired that an absorbent layer 40 formed of HIPE foam have a caliper (prior to wetting) that provides satisfactory volume to a standard-sized pad. Of course, a relatively thick pad can be manufactured, but that is typically deemed undesirable for daytime use in view of desires for flexibility/pliability and thinness, for comfort and discreetness under clothing. The manufacture must balance these competing objectives. Accordingly a feminine hygiene pad with a HIPE foam absorbent layer as contemplated herein, it may be desired that the layer have a caliper in the majority of its wearer-facing surface area (prior to wetting) of 1 mm to 5 mm, or more preferably 1.5 mm to 3.5 mm, or even more preferably 2.0 mm to 3.0 mm. (The caliper of a HIPE foam layer may be measured visually, with assistance of magnification/microscopy and/or photography or any other facilitating techniques and equipment, to any extent deemed useful.) Where the absorbent layer 40 includes two sublayers 40a, 40b as described herein, it may be desired that the upper sublayer 40a have a caliper (prior to wetting) of 0.64 mm to 3.2 mm, or preferably 0.96 mm to 2.24 mm, or even more preferably 1.28 mm to 1.92 mm; and it may be desired that the lower sublayer 40b have a caliper (prior to wetting) of 0.16 mm to 0.80 mm, or more preferably 0.24 mm to 0.56 mm, or even more preferably 0.32 mm to 0.48 mm.

Absorbency Properties and Interface Between Topsheet and Absorbent Layer

The affinity and absorbency of an absorbent/hydrophilic structure for an aqueous fluid may be characterized in part by its capillary absorption pressure. Capillary absorption pressure (CAP), may be measured according to steps in the Capillary Work Potential measurement method set forth below. It is a value that reflects the magnitude of the tendency of the structure to draw in aqueous fluid. It will be appreciated that a plot of the CAP of an absorbent structure vs. saturation level will have an initial maximum value (at the outset of absorption of fluid) and decrease as the structure draws in fluid and approaches its full absorption capacity, i.e., full saturation.

The resistance to desorption, or the tendency of an absorbent/hydrophilic structure to retain absorbed fluid, may be characterized in part by its capillary desorption pressure (CDP). CDP, which also may be measured according to steps in the Capillary Work Potential measurement method set forth below, is a value that reflects the magnitude of pressure (or pressure differential) required to drive (or draw) out aqueous fluid absorbed and held in the structure. It will be appreciated that a plot of the CDP of a structure vs. saturation level will have an initial minimum value (prior to exit of any fluid from the structure), and increase as the fluid leaves it.

CAP and CDP of a given structure are a function of the extent of hydrophilicity of the solid surfaces within the structure, the average size of the interstitial spaces or voids, cells or pores within the structure among/between the solid surfaces, and the number of the interstitial spaces, cells or pores within the structure per unit volume of the structure.

In order for a layered topsheet/absorbent layer combination to be able to effectively move discharged fluid from the top surface of the topsheet in a z-direction direction away from the wearer, in addition to other conditions described herein, the CAP of the absorbent layer must be greater than the CDP of the topsheet, at a selected level of absorbed fluid content of the topsheet, preferably a relatively low level. In order for a layered topsheet/absorbent layer combination to be able to move discharged fluid in a z-direction direction away from the wearer with acceptable rapidity, i.e., such that the topsheet does not have time to excessively wick and thereby distribute (i.e. spread) discharged fluid along planar directions (creating an undesirably large stain on the topsheet) and does not feel overly wet to the wearer shortly following a discharge of fluid thereon, the capillary absorption pressure of the absorbent layer at, e.g., a 20 percent saturation should be greater than the capillary desorption pressure of the topsheet at the same saturation, where percent saturation is the percent of total pore volume of the material that is occupied by the fluid, and the test fluid is saline solution as specified in the Capillary Work Potential measurement method set forth below.

The total absorbency of a given material structure may be further characterized by its capillary work potential in absorption mode (CWPA) and drainage or desorption mode (CWPD), as measured using the Capillary Work Potential measurement method set forth below. CWPA is a measure of the work that an absorbent material will perform in drawing in a quantity of aqueous fluid under conditions of the described method. CWPD is a measure of the work necessary to expel or draw away aqueous fluid absorbed and held by a structure under conditions of the described method. For a given structure that is hydrophilic and absorbent of aqueous fluid, the CWPD will be greater than the CWPA because the properties of an absorbent structure (hydrophilicity; cell/pore size and volume) cause it to tend to retain fluid. CWPA and CWPD of a given structure are affected by the features and properties that affect CAP and CDP, and also by the total volume of the interstitial spaces or voids, cells or pores within the structure within the structure. Thus, it will be appreciated that CWPA and CWPD of a structure are in part affected by the total volume (i.e., size) of the structure.

In order to ensure that the absorbent layer 40 will drain the topsheet 20 of fluid absorbed by the topsheet sufficiently for the two to provide a satisfactory pad, the absorbent layer should have a CWPA that is greater than the CWPD of the topsheet. If this condition is not satisfied, the absorbent layer will not sufficiently drain fluid from the topsheet to both (1) ensure that the topsheet will not retain an unacceptably wet feeling following a discharge; and (2) ensure that the topsheet is kept drained and has capacity to accept successive discharges of fluid over a reasonable time of use of the pad 10.

It has been discovered that an absorbent layer formed of HIPE foam as described herein may be manufactured to have a capillary absorption pressure great enough to draw fluid from an absorbent cotton topsheet with acceptable rapidity over repeated discharges, i.e., over a reasonable time of use of the pad.

In examples in which the topsheet is formed of a hydrophilic and absorbent web material, the topsheet material may tend to retain fluid on its wearer-facing and outward-facing surfaces, and within the interstitial spaces between and along the surfaces of the fibers of the web material, unless the underlying material has absorption capacity and absorption pressure greater than the desorption pressure of the topsheet, as described above; and there is sufficient direct contact maintained between the topsheet and the underlying absorbent layer to enable the fluid to move from fiber surfaces within the topsheet structure, directly to surfaces of material within the underlying absorbent layer structure, such that the underlying absorbent layer may draw the fluid from the topsheet. Prior to the time it is fully saturated, an absorbent material will not release absorbed fluid unless an adjacent material with greater affinity for the fluid is in sufficient direct contact. Accordingly, it is important to provide structure sufficient to maintain sufficient contact, without obstructing fluid movement. No intervening layer or structure of material, or at least no intervening layer or structure of material less absorbent than the topsheet or more absorbent than the absorbent layer, should be interposed between the material of the topsheet 20 and the material of the absorbent layer 40, at least within the bonding region 25, more preferably over a majority of the wearer-facing surface area of the absorbent layer 40, and even more preferably over the entirety of the wearer-facing surface area of the absorbent layer 40—unlike systems provided in many current feminine hygiene pads, which include a distinct fluid acquisition/distribution material layer between the topsheet and the absorbent materials of the absorbent core.

In some examples, sufficient direct contact between the topsheet 20 and the absorbent layer 40 may be effected by deposit(s) of adhesive between the topsheet and the absorbent layer, adhesively bonding them in close z-direction proximity. The adhesive may be applied in a pattern or arrangement of adhesive deposits interspersed with areas in which no adhesive is present (unbonded areas), such that the adhesive holds the two layers in close z-direction proximity, while areas remain in which no adhesive is present to obstruct z-direction fluid movement between the layers.

Figure 3A:
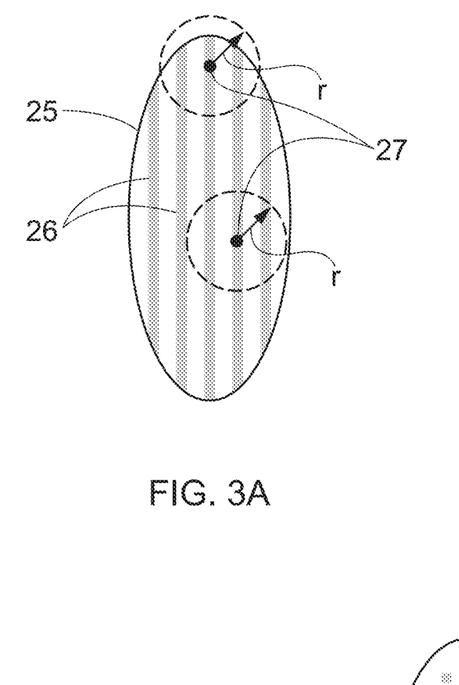
FIGS. 3A-3C are plan views of several examples of adhesive deposit patterns within a bonding region, in which a topsheet may be bonded to an absorbent layer.
Figure 3B:
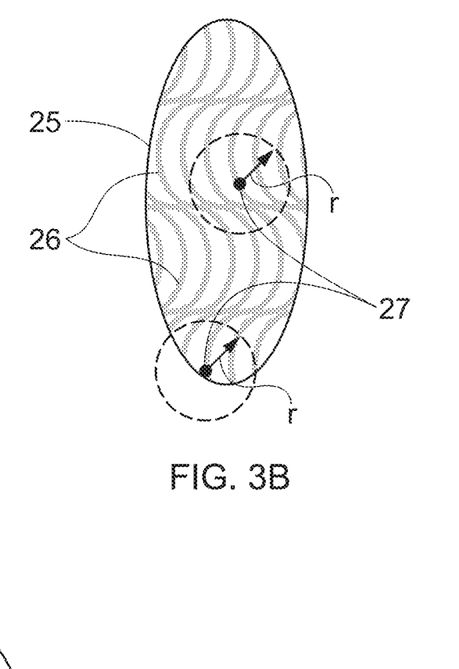
Figure 3C:
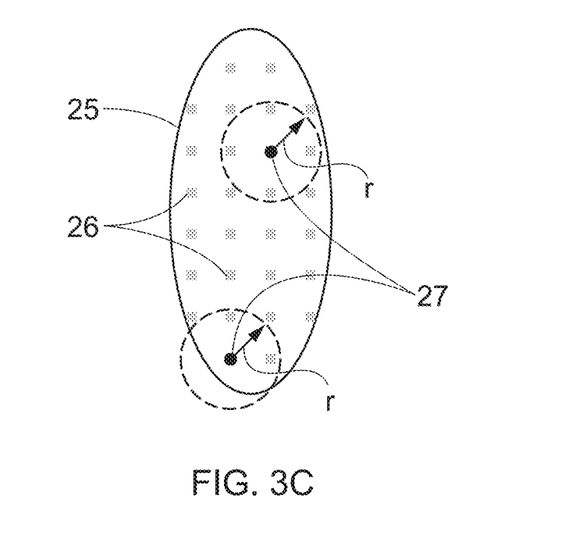

Referring to FIGS. 1 and 3A-3C, to ensure that the topsheet and absorbent layer are held in sufficiently close z-direction proximity at least in the area of the topsheet expected to receive a discharge of fluid, it may be desired to dispose a bonding region 25 on the pad at a location that includes the intersection of the longitudinal and lateral axes 100, 200. The bonding region 25 should be of sufficient size to be reliably present beneath the expected discharge location when the pad is in use, with reasonably minor variations of placement by the wearer within the underpants; accordingly, it may be desired that the bonding region have an area of at least 15 cm$^2$, more preferably at least 30 cm$^2$. Even more preferably, it may be desired that the bonding region have an area that is at least half of the total wearer-facing surface area of the absorbent layer. (Note: FIGS. 3A-3C are not presented herein as actual size or scale depictions.)

To ensure that the topsheet 20 and the absorbent layer remain in sufficient z-direction proximity during use, it may be desired that, within any identifiable first point location 27 within the bonding region, at which the topsheet is bonded to the absorbent layer, there is a second point location at which the topsheet is bonded to the absorbent layer, within a 10 mm radius, more preferably within a 6 mm radius, 5 mm radius, 4 mm radius, and even more preferably with a 3 mm radius r of the first point location. Referring to FIGS. 3A-3C, depicting three non-limiting examples, it can be seen that a variety of patterns or arrangements of bonds (via adhesive deposits 26 or other bonding mechanisms) may be employed to impart this feature. Within radius r of each point location 27, there are a number of additional point locations where bonding between the topsheet and the absorbent layer is present in the examples depicted.

It will be appreciated that a continuous deposit of adhesive may be applied to bond the topsheet and the absorbent layer within the entirety of bonded region 25, but that such a continuous deposit of adhesive could form a barrier that would obstruct the movement of fluid from the topsheet to the absorbent layer. Accordingly, it is preferable that, in examples in which the bonding mechanism is deposits of adhesive, the deposits are disposed in a pattern or arrangement that is discontinuous or intermittent such that it creates bonded areas interspersed with unbonded areas between the topsheet and the absorbent layer. Additionally, when the absorbent layer is formed of an open-celled foam (such as a HIPE foam contemplated herein) it may be desired that the adhesive selected not effect adhesion to the absorbent layer via chemical, dispersive or diffusive adhesion with the foam layer at the adhesive deposit locations, but rather, that it effect adhesion to the foam layer mechanically, by flowing to a limited extent into the cells, at least partially assuming the shapes thereof, and solidifying in such position to form mechanical interlocks with the cell structures, which enable the adhesive to hold the topsheet to the absorbent layer. Such an adhesive may be preferred so as not to alter the molecular structure or composition of the foam material, potentially negatively affecting its fluid absorption properties or mechanical strength. In one example, a suitable adhesive for use with a HIPE foam may be H1750 hot melt adhesive from Bostik, Wauwatosa, Wisc. (currently a subsidiary of Arkema, Columbes, France).

Unapertured topsheets for feminine hygiene pads formed of nonwoven web material and including or consisting predominately of hydrophilic fibers (such as cotton fibers) are known and have been included with some feminine hygiene products to date. (Herein, an "unapertured" nonwoven topsheet is one in which a majority of its surface area has not been subjected to any process that creates an arrangement of holes or apertures entirely therethrough, that persist prior to wetting of the topsheet, of an average size (greatest dimension) greater than 0.5 mm along an x-y planar direction.) Although favored by some consumers for their natural/plant-based material origin, cotton-based topsheets have been disfavored by other consumers as a result of their substantial absorbency, i.e., capillary absorption and desorption pressures, causing them to resist drainage by conventionally included acquisition/distribution and absorbent layer structures. Following a discharge of menstrual fluid, a pad with a cotton-based topsheet overlying a conventional absorbent structure can feel to the user like a wet cloth held against the skin for an extended time period, which many users find objectionable. This dilemma has been present for many years, and to the inventor's knowledge, has not previously been satisfactorily addressed.

It has been discovered, however, that a non-apertured hydrophilic fiber topsheet (such as a cotton-based topsheet) overlaid in direct, sufficient face-to-face proximate relationship with a HIPE foam absorbent layer or other layer adapted/manufactured to have capillary absorption capability sufficient to draw fluid from the topsheet, without any intervening less absorbent layers and in combination with other structural features as described herein, will be substantially drained of fluid by the absorbent layer, and regain a much drier feel against the skin following a discharge. It has been discovered that a suitably composed and manufactured HIPE foam absorbent layer as described herein, for example, has a greater affinity for menstrual fluid than such a topsheet, and thereby, has the capability to draw and retain fluid away from the topsheet when the two are disposed and held in sufficiently effective proximate, contacting relationship with each other. When the absorbent layer has a sufficient volume, it can serve this function over a reasonably suitable time of use of the pad.

Backsheet

The backsheet 30 may be positioned adjacent an outward-facing surface of the absorbent layer 40 and may be joined thereto by any suitable attachment methods. For example, the backsheet 30 may be secured to the absorbent layer 40 by a uniform continuous layer of adhesive, a patterned layer of adhesive, or an array of separate lines, spirals, or spots of adhesive. Alternatively, the attachment method may include heat bonds, pressure bonds, ultrasonic bonds, dynamic mechanical bonds, or any other suitable attachment mechanisms or combinations thereof. In other examples, it is contemplated that the absorbent layer 40 is not joined directly to the backsheet 30.

The backsheet 30 may be impervious, or substantially impervious, to liquids (e.g., urine, menstrual fluid) and may be manufactured from a thin plastic film, although other flexible liquid impervious materials may also be used. As used herein, the term "flexible" refers to materials which are compliant and will readily conform to the general shape and contours of the human body. The backsheet 30 may prevent, or at least substantially inhibit, fluids absorbed and contained within the absorbent layer 40 from escaping and reaching articles of the wearer's clothing which may contact the pad 10 such as underpants and outer clothing. However, in some instances, the backsheet 30 may be made and/or adapted to permit vapor to escape from the absorbent layer 40 (i.e., the backsheet is made to be breathable), while in other instances the backsheet 30 may be made so as not to permit vapors to escape (i.e., it is made to be non-breathable). Thus, the backsheet 30 may comprise a polymeric film such as thermoplastic films of polyethylene or polypropylene. A suitable material for the backsheet 30 is a thermoplastic film having a thickness of from about 0.012 mm (0.5 mil) to about 0.051 mm (2.0 mils), for example. Any suitable backsheet known in the art may be utilized with the present invention.

Some suitable examples of backsheets are described in U.S. Pat. Nos. 5,885,265; 4,342,314; and 4,463,045. Suitable single layer breathable backsheets for use herein include those described for example in GB A 2184 389; GB A 2184 390; GB A 2184 391; U.S. Pat. Nos. 4,591,523, 3,989,867, 3,156,242; WO 97/24097; U.S. Pat. Nos. 6,623, 464; 6,664,439 and 6,436,508.

The backsheet may have two layers: a first layer comprising a vapor permeable aperture-formed film layer and a second layer comprising a breathable microporous film layer, as described in U.S. Pat. No. 6,462,251. Other suitable examples of dual or multi-layer breathable backsheets for use herein include those described in U.S. Pat. Nos. 3,881, 489, 4,341,216, 4,713,068, 4,818,600; EP 203 821, EP 710 471; EP 710 472, and EP 0 793 952.

Test/Measurement Methods

Capillary Work Potential via Pore Volume Distribution

Pore Volume Distribution determines the estimated porosity of the effective pores within a porous sample by measuring the fluid movement into and out of said sample as stepped, controlled differential pressure is applied to the sample in a sample chamber. The incremental and cumulative quantity of fluid that is thereby absorbed/drained by the porous sample at each pressure is then determined. In turn, work done by the porous sample normalized by the area of said sample is calculated as Capillary Work Potential.

Method Principle

For uniform cylindrical pores, the radius of a pore is related to the differential pressure required to fill or empty the pore by the following equation:

$$\text{Differential Pressure} = [2\gamma \cos \Theta]/r$$

where γ=liquid surface tension, ☉=contact angle, and r=pore radius.

Pores contained in natural and manufactured porous materials are often thought of in terms such as voids, holes or conduits, and these pores are generally not perfectly cylindrical nor all uniform. One can nonetheless use the above equation to relate differential pressure to an effective pore radius, and by monitoring liquid movement into or out of the material as a function of differential pressure, characterize the effective pore radius distribution in said porous material.

(Because nonuniform pores are approximated as uniform by the use of an effective pore radius, this general methodology may not produce results precisely in agreement with measurements of void dimensions obtained by other methods such as microscopy.)

The Pore Volume Distribution method uses the above principle and is reduced to practice using the apparatus and approach described in "Liquid Porosimetry: New Methodologies and Applications" by B. Miller and I. Tyomkin published in The Journal of Colloid and Interface Science (1994), volume 162, pages 163-170, incorporated herein by reference. This method relies on measuring the increment of liquid volume that enters or leaves a porous sample as the differential air pressure is changed between ambient ("lab") air pressure and a slightly elevated air pressure (positive differential pressure) surrounding the sample in a sample test chamber. The sample is introduced to the sample chamber dry, and the sample chamber is controlled at a positive differential pressure (relative to the lab) sufficient to prevent fluid uptake into the sample after the fluid bridge is opened. After opening the fluid bridge, the differential air pressure is decreased in steps to 0, and in this process subpopulations of pores within the sample acquire liquid according to their effective pore radius. After reaching a minimal differential pressure at which the mass of fluid within the sample is at a maximum, differential pressure is increased stepwise again toward the starting pressure, and the liquid is drained from the sample. The absorption portion of the stepped sequence begins at the maximum differential pressure (smallest corresponding effective pore radius) and ends at the minimum differential pressure (largest corresponding effective pore radius). The drainage portion of the sequence begins at the minimum pressure differential and ends at the maximum pressure differential. After correcting for any fluid movement for each particular pressure step measured on the chamber while empty for the entire absorption/drainage sequence, the fluid uptake by the sample (mg) as well as cumulative volume (mm$^3$/mg) at each differential pressure is determined in this method.

Sample Conditioning and Sample Preparation

The Pore Volume Distribution method is conducted on samples that have been conditioned for at least 2 hours in a room maintained at a temperature of 23° C.±2.0° C. and a relative humidity of 50%±2%, and all tests are conducted under the same environmental conditions in such conditioned room. Any damaged product or sample that has defects such as wrinkles, tears, holes, and similar are not tested. A sample conditioned as described herein is considered dry for purposes of this invention. Determine which side of the sample is intended to face the wearer in use, then cut it to 55 mm long by 55 mm wide. Measure the mass of the sample and record to the nearest 0.1 mg. Three samples are measured for any given material being tested, and the results from those three replicates are averaged to give the final reported values.

Apparatus

Apparatus suitable for this method is described in "Liquid Porosimetry: New Methodology and Applications" by B. Miller and I. Tyomkin published in The Journal of Colloid and Interface Science (1994), volume 162, pages 163-170. Further, any pressure control scheme capable of controlling the sample chamber pressure between 0 mm H$_2$0 and 1098 mm H$_2$0 differential pressure may be used in place of the pressure-control subsystem described in this reference. One example of a suitable overall instrumentation and software is the TRI/Autoporosimeter (Textile Research Institute (TRI)/Princeton Inc. of Princeton, NJ, USA). The TRI/Autoporosimeter is an automated computer-controlled instrument for measuring pore volume distributions in porous materials (e.g. the volumes of different size pores within the range from 5 μm to 1200 μm effective pore radii). Computer programs such as Automated Instrument Software Releases 2000.1 or 2003.1/2005.1 or 2006.2; or Data Treatment Software Release 2000.1 (available from TRI Princeton Inc.), and spreadsheet programs may be used to capture and analyze the measured data.

Figure 4:
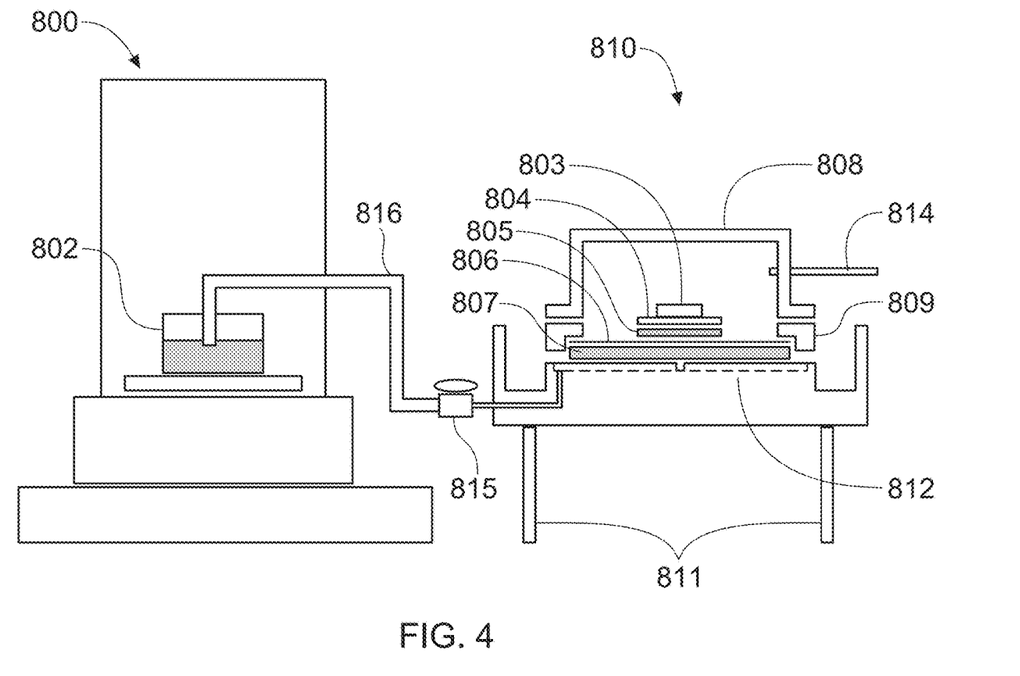
FIG. 4 is a schematic illustration of a configuration of equipment for use in the capillary work potential measurement method set forth below.

A schematic depiction of suitable equipment is shown in FIG. 4. The equipment consists of a balance 800 with fluid reservoir 802 which is in direct fluid communication with the sample 805 which resides in a sealed, air-pressurized sample chamber 810. The fluid communication between the reservoir 802 and the sample chamber 810 is controlled by valve 815. A weight 803 placed on top of a Plexiglass plate 804 (55 mm long by 55 mm wide) is used to apply a confining pressure of 0.25 psi on the test sample to ensure good contact between the sample and a fluid saturated membrane 806 throughout the test. The membrane 806 (90 mm diameter, 150 um thick, 1.2 μm pore size; mixed cellulose ester filter RAWP09024; available from Millipore Corporation of Bedford, MA) is attached to a macro-porous frit 807 (Monel plate with 90 mm diameter, 60 mm thick; available from Mott Corporation, Farmington, CT, or equivalent) as follows. Adhere the membrane 806 to the frit 807 using Krylon® spray paint (Gloss White Spray Paint #1501; available from FilmTools, or equivalent) as the adhesive. Allow the prepared membrane/frit assembly to dry prior to use.

To prepare the equipment for testing, fill the inner base 812 of the sample chamber 810 with test fluid. The test fluid is degassed 0.9% saline solution, prepared by adding 9.0 g of reagent grade NaCl per 1 L of deionized water (liquid density is 1.01 g/cm$^3$, surface tension γ to be 72.3±1 mN/m, contact angle cos ☉=0.37). Place the membrane/frit assembly, membrane 806 side up, onto the inner base 812 of the sample chamber 810, and secure it into place with a locking collar 809. Fill the reservoir 802 and connecting tube 816 with test fluid. Open valve 815 and ensure that no air bubbles are trapped within the connecting tube or the pores within the membrane/frit assembly. Using the legs 811 of the sample chamber 810, level the sample chamber and adjust the height of the sample chamber (and/or the amount of fluid in the reservoir 802) as necessary, to bring the top surface of the membrane 806 into the same horizontal plane as the top surface of the fluid in the reservoir 802.

Program the system to progress through a sequence of stepped differential pressures (in mm H$_2$0) as follows: 1098, 549, 366, 275, 220, 183, 137, 110, 92, 78, 69, 61, 55, 50, 46, 42, 39, 37, 34, 32, 31, 29, 27, 24, 22, 20, 18, 14, 9.2, 6.9, 5.5, 4.6, 5.5, 6.9, 9.2, 14, 18, 20, 22, 24, 27, 29, 31, 32, 34, 37, 39, 42, 46, 50, 55, 61, 69, 78, 92, 110, 137, 183, 220, 275, 366, 549, 1098. These pressures correlate to effective pore radii from 5 μm (1098 mm H$_2$0) to 1200 μm (4.6 mm H$_2$0). The criterion for moving from one pressure step to the next is that fluid uptake/drainage to/from the sample, measured at the balance 800, is less than 10 mg/min for 15 seconds.

Method Procedure

Check the system for leaks and ensure the maximum test pressure can be reached as follows. With liquid valve 815 open, place the top 808 of the sample chamber 810 in place and seal the chamber. Apply sufficient air pressure to the chamber 810 (via connection 814) to achieve a differential pressure of 1098 mm H$_2$O (5 µm effective pore radius). Close the liquid valve 815 then open the sample chamber. Place the sample 805 (wearer side facing down) directly onto the membrane 806, then place the cover plate 804 and confining weight 803 centered over the sample. Replace the top 808 and reseal the sample chamber 810. Open the liquid valve 815 to allow movement of fluid between the liquid reservoir 802 and the sample and start the test to progress through the pre-specified sequence of differential pressures. The amount of fluid absorbed (or drained) by the sample at each pressure step over the entire sequence is recorded as Uptake to the nearest 0.1 mg.

A separate "blank" measurement is performed by following this same method procedure (same stepped sequence of differential pressures) on an empty sample chamber with no sample 805, cover plate 804 or confining weight 803 present on the membrane/frit assembly. Any fluid movement observed is recorded (mg) at each of the pressure steps. Fluid uptake data for the sample are corrected for any fluid movement associated with the empty sample chamber by subtracting fluid uptake values of this "blank" measurement from corresponding values in the measurement of the sample, and recorded as Blank Corrected Sample Uptake to the nearest 0.1 mg.

Determination of Capillary Pressure, Cumulative Volume and Capillary Work Potential The % Saturation of the sample at each of the pressure steps for both the absorption and drainage portions of the test sequence can be calculated by dividing the maximum Blank Corrected Sample Uptake (mg) by the Blank Corrected Sample Uptake (mg), then multiplying by 100. From the data collected across the entire sequence, one of average skill in the art can then determine the % Saturation at any given capillary absorption pressure (CAP) or capillary desorption (drainage) pressure (CDP). The CAP and CDP are reported to the nearest 0.1 mm H$_2$O for any specified % Saturation.

The cumulative volume is calculated for each of the pressure steps by the following equation:

Cumulative Volume (mm$^3$/mg)=Blank Corrected Sample Uptake (mg)/Fluid Density (g/cm$^3$)/ Mass of Sample (mg)

The Capillary Work Potential (CWP) is the work done by the sample normalized by the area of the sample. The trapezoidal rule is used to integrate the ith Pressure as a function of Cumulative Volume over n data points for the absorption and drainage portions of the cycle.

$$CWP\left[\frac{mJ}{m^2}\right] = \frac{W}{A_w} = \sum_{i=1}^{n} \frac{1}{2} \frac{m_w(CV_{i+1} - CV_i)(P_i + P_{i+1})}{A_w}\left(10^3\left[\frac{mJ}{J}\right]\right)$$

where
$m_w$=mass of sample (mg)
CV=Cumulative Volume (m$^3$/mg)
P=Air Pressure (Pa)
$A_w$=Area of sample on one side (m$^2$)
Report the CWP, CWPA and CWPD to the nearest 0.1 mJ/m$^2$, where CWPA represents the absorption portion of the pressure sequence and CWPD represents the drainage portion of the pressure sequence.

Nonwoven Web Caliper Measurement

The caliper, or thickness, of a test sample of a nonwoven web material is measured as the distance between a reference platform on which the sample rests and a pressure foot that exerts a specified amount of pressure onto the sample over a specified amount of time. All measurements are performed in a laboratory maintained at 23° C.±2 C.° and 50%±2% relative humidity and test samples are conditioned in this environment for at least 2 hours prior to testing.

Caliper is measured with a manually-operated micrometer equipped with a pressure foot capable of exerting a steady pressure of 2.0 kPa±0.01 kPa onto the test sample. The manually-operated micrometer is a dead-weight type instrument with readings accurate to 0.001 mm. A suitable instrument is Mitutoyo Series 543 ID-C Digimatic, available from VWR International, or equivalent. The pressure foot is a flat ground circular movable face with a diameter that is smaller than the test sample and capable of exerting the required pressure. A suitable pressure foot has a diameter of 25.4 mm, however a smaller or larger foot can be used depending on the size of the sample being measured. The test sample is supported by a horizontal flat reference platform that is larger than and parallel to the surface of the pressure foot. The system is calibrated and operated per the manufacturer's instructions.

Obtain a test sample, if necessary by removing it from an absorbent article. When excising the test sample from an absorbent article, use care to not impart any contamination or dimensional deformation to the test sample. The test sample is obtained from an area free of folds or wrinkles, and it must be larger than the pressure foot.

To measure caliper, first zero the micrometer against the horizontal flat reference platform. Place the test sample on the platform with the test location centered below the pressure foot. Gently lower the pressure foot with a descent rate of 3.0 mm±1.0 mm per second until the full pressure is exerted onto the test sample. Wait 5 seconds and then record the caliper of the test sample to the nearest 0.01 mm. In like fashion, repeat for a total of five replicate test samples. Calculate the arithmetic mean for all caliper measurements and report as Web Caliper to the nearest 0.01 mm.

In view of the foregoing disclosure, the following non-limiting examples are contemplated:

1. A feminine hygiene pad comprising a liquid-permeable topsheet, a liquid-impermeable backsheet, and an absorbent layer disposed between the topsheet and the backsheet,
   wherein the topsheet comprises a fibrous nonwoven web material comprising hydrophilic fibers;
   wherein the absorbent layer comprises an open-celled foam formed through polymerization of a HIPE;
   wherein the topsheet and the absorbent layer are disposed in direct face-to-face relationship with each other, and attached to each other within a bonding region of at least 15 cm$^2$, more preferably at least 30 cm$^2$, and even more preferably at least half of a surface area of a wearer-facing surface of the absorbent layer wherein within the bonding region, each first identifiable point of attachment between the topsheet and the absorbent layer has a neighboring second identifiable point of attachment between the topsheet and the absorbent layer within a 6 mm radius of the first identifiable point of attachment.

2. A feminine hygiene pad comprising a liquid-permeable topsheet, a liquid-impermeable backsheet, and an absorbent layer disposed between the topsheet and the backsheet,
   wherein the topsheet comprises a fibrous nonwoven web material comprising cotton fibers and having a CWPD;
   wherein the absorbent layer has a CWPA greater than the CWPD, and has a caliper (prior to wetting) of 1 mm to 5 mm, or more preferably 1.5 mm to 3.5 mm, or even more preferably 2.0 mm to 3.0 mm;
   wherein the topsheet and the absorbent layer are disposed in direct face-to-face relationship with each other, and attached to each other within a bonding region of at least 15 cm$^2$, more preferably at least 30 cm$^2$, and even more preferably at least half of a surface area of a wearer-facing surface of the absorbent layer wherein within the bonding region, each first identifiable point of attachment between the topsheet and the absorbent layer has a neighboring second identifiable point of attachment between the topsheet and the absorbent layer within a 6 mm radius of the first identifiable point of attachment.

3. The feminine hygiene pad of either of examples 1 or 2 wherein attachment between the topsheet and the absorbent layer is effected by adhesive discontinuously or intermittently deposited so as to form bonded areas while leaving interspersed unbonded areas between the topsheet and the absorbent layer within the bonding region.

4. The feminine hygiene pad of any of the preceding examples wherein the nonwoven web material comprises plant fibers.

5. The feminine hygiene pad of any of the preceding examples wherein the nonwoven web material comprises cotton fibers.

6. The feminine hygiene pad of any of the preceding examples wherein the nonwoven web material comprises rayon fibers.

7. The feminine hygiene pad of example 4 wherein the nonwoven web material comprises predominately plant fibers, preferable substantially entirely plant fibers.

8. The feminine hygiene pad of example 5 wherein the nonwoven web material comprises predominately cotton fibers, preferably substantially entirely cotton fibers.

9. The feminine hygiene pad of example 6 wherein the nonwoven web material comprises predominately rayon fibers, preferably substantially entirely rayon fibers.

10. The feminine hygiene pad of any of examples 4-9 wherein the nonwoven web material also comprises fibers spun from thermoplastic polymeric resin.

11. The feminine hygiene pad of any of examples 4-10 wherein the nonwoven web material has been hydroentangled.

12. The feminine hygiene pad of any of the preceding examples wherein the absorbent layer comprises at least two absorbent sublayers comprising a relatively larger-celled, wearer-facing sublayer disposed in contact with a relatively smaller-celled, outward-facing sublayer.

13. The feminine hygiene pad of any of the preceding examples wherein the fibrous nonwoven web material has a CWPD and the absorbent layer has a CWPA, and the CWPA is greater than the CWPD, and the absorbent layer has a caliper (prior to wetting) of 1 mm to 5 mm, or more preferably 1.5 mm to 3.5 mm, or even more preferably 2.0 mm to 3.0 mm.

14. The feminine hygiene pad of example 13 wherein the CWPA is greater than the CWPD by at least 40 mJ/m$^2$, more preferably at least 45 mJ/m$^2$, and even more preferably at least 50 mJ/m$^2$.

15. The feminine hygiene pad of any of the preceding examples wherein the fibrous nonwoven web material has a basis weight of 20 gsm to 50 gsm, more preferably 25 gsm to 45 gsm, and even more preferably 30 gsm to 40 gsm.

16. The feminine hygiene pad of example 15 wherein the fibrous nonwoven web material has a caliper of 0.20 mm to 0.60 mm, more preferably 0.25 mm to 0.55 mm, and even more preferably 0.30 mm to 0.45 mm.

17. The feminine hygiene pad of either of examples 15 or 16 wherein the fibrous nonwoven web material comprises cotton fibers and has a density of 74 kg/m$^3$ to 110 kg/m$^3$ and more preferably 83 kg/m$^3$ to 101 kg/m$^3$.

18. The feminine hygiene pad of any of the preceding examples wherein the absorbent layer comprises an arrangement of perforations present in at least the bonding region.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety to the extent not inconsistent herewith and unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A feminine hygiene pad comprising a liquid-permeable topsheet, a liquid-impermeable backsheet, and an absorbent layer disposed between the topsheet and the backsheet,
   wherein the topsheet comprises a fibrous nonwoven web material comprising hydrophilic fibers;
   wherein the absorbent layer comprises a layer of open-celled foam formed through polymerization of a HIPE, the foam comprising a wearer-facing sublayer having a first average cell size, disposed in contact with an outward-facing sublayer having a second average cell size that is smaller than the first average cell size;
   wherein the topsheet and the open-celled foam layer are disposed in direct face-to-face relationship with each other, and attached to each other within a bonding region of at least 15 cm$^2$, wherein within the bonding region, each first identifiable point of attachment between the topsheet and the absorbent layer has a neighboring second identifiable point of attachment between the topsheet and the absorbent layer within a 6 mm radius of the first identifiable point of attachment;
   wherein the bonding region overlies an intersection of longitudinal and lateral axes of the pad;

wherein attachment within the bonding region is effected by adhesive discontinuously or intermittently deposited so as to form bonded areas while leaving interspersed unbonded areas between the topsheet and the absorbent layer within the bonding region; and wherein the topsheet is unapertured.

2. The feminine hygiene pad of claim 1 wherein the nonwoven web material comprises cotton fibers.

3. The feminine hygiene pad of claim 2 wherein the nonwoven web material comprises predominately cotton fibers.

4. The feminine hygiene pad of claim 3 wherein the fibrous nonwoven web material has a basis weight of 20 gsm to 50 gsm.

5. The feminine hygiene pad of claim 4 wherein the fibrous nonwoven web material has a caliper of 0.20 mm to 0.60 mm.

6. The feminine hygiene pad of claim 3 wherein the absorbent layer comprises an arrangement of perforations present in at least the bonding region.

7. The feminine hygiene pad of claim 2 wherein the nonwoven web material also comprises fibers spun from thermoplastic polymeric resin.

8. The feminine hygiene pad of claim 2 wherein the nonwoven web material has been hydroentangled.

9. A feminine hygiene pad comprising a liquid-permeable topsheet, a liquid-impermeable backsheet, and an absorbent layer disposed between the topsheet and the backsheet, wherein the topsheet comprises a fibrous nonwoven web material comprising cotton fibers and having a capillary work potential in desorption mode (CWPD);

wherein the absorbent layer comprises a layer of open-celled foam formed through polymerization of a HIPE, the foam comprising a wearer-facing sublayer having a first average cell size, disposed in contact with an outward-facing sublayer having a second average cell size that is smaller than the first average cell size;

wherein the absorbent layer has a capillary work potential in absorption mode (CWPA) greater than the CWPD, and has a caliper (prior to wetting) of 1 mm to 5 mm;

wherein the topsheet and the open-celled foam layer are disposed in direct face-to-face relationship with each other, and attached to each other within a bonding region of at least 15 cm$^2$, wherein within the bonding region, each first identifiable point of attachment between the topsheet and the absorbent layer has a neighboring second identifiable point of attachment between the topsheet and the absorbent layer within a 6 mm radius of the first identifiable point of attachment;

wherein the bonding region overlies an intersection of longitudinal and lateral axes of the pad;

wherein attachment within the bonding region is effected by adhesive discontinuously or intermittently deposited so as to form bonded areas while leaving interspersed unbonded areas between the topsheet and the absorbent layer within the bonding region; and wherein the topsheet is unapertured.

10. The feminine hygiene pad of claim 9 wherein the nonwoven web material comprises predominately cotton fibers.

11. The feminine hygiene pad of claim 9 wherein the nonwoven web material also comprises fibers spun from thermoplastic polymeric resin.

12. The feminine hygiene pad of claim 9 wherein the nonwoven web material has been hydroentangled.

13. The feminine hygiene pad of claim 9 wherein the fibrous nonwoven web material has a basis weight of 20 gsm to 50 gsm.

14. The feminine hygiene pad of claim 13 wherein the fibrous nonwoven web material has a caliper of 0.20 mm to 0.60 mm.

15. The feminine hygiene pad of claim 9 wherein the absorbent layer comprises an arrangement of perforations present in at least the bonding region.

* * * * *